(12) United States Patent
Williams

(10) Patent No.: US 7,500,851 B2
(45) Date of Patent: Mar. 10, 2009

(54) MAXILLARY ARCH EXPANDER UNBANDED TO TEETH

(76) Inventor: Michael O. Williams, 424 Courthouse Rd., Gulfport, MO (US) 39507

(*) Notice: Subject to any disclaimer, the term of this patent is extended or adjusted under 35 U.S.C. 154(b) by 0 days.

(21) Appl. No.: 11/480,681

(22) Filed: Jul. 1, 2006

(65) Prior Publication Data
US 2008/0003535 A1 Jan. 3, 2008

(51) Int. Cl.
*A61C 31/00* (2006.01)
(52) U.S. Cl. .............................. 433/7; 433/18
(58) Field of Classification Search ............... 433/7, 433/18
See application file for complete search history.

(56) References Cited

U.S. PATENT DOCUMENTS

| | | | |
|---|---|---|---|
| 4,347,054 A | 8/1982 | Kraus et al. | |
| 4,482,318 A | 11/1984 | Forster | |
| 4,917,601 A | 4/1990 | Williams | |
| 5,472,344 A | 12/1995 | Binder et al. | |
| 5,645,422 A | 7/1997 | Williams | |
| 5,902,304 A * | 5/1999 | Walker et al. | 606/71 |
| 5,919,042 A | 7/1999 | Williams | |
| 6,328,745 B1 * | 12/2001 | Ascherman | 606/86 |
| 2004/0009449 A1 * | 1/2004 | Mah et al. | 433/7 |
| 2005/0186524 A1 * | 8/2005 | Abolfathi et al. | 433/7 |

* cited by examiner

*Primary Examiner*—John J Wilson
*Assistant Examiner*—Heidi M Eide
(74) *Attorney, Agent, or Firm*—Paul M. Denk

(57) ABSTRACT

An orthodontic arch expander joins to a mouthpiece proximate to the rear of the mouthpiece. The transparent mouthpiece has a desired arc that fits over the teeth of the upper jaw. The mouthpiece has two wings that join near the incisors and then become parallel and spaced apart around the molars. Near the molars, an arch expander joins to the mouth piece. The arch expander has two telescoping shells with a threaded jack and cooperating springs. Each shell joins to a corresponding wing of the mouthpiece. Turning the jack lengthens a rod that pushes the shells outwards against the mouthpiece thus widening the maxillary arch without brackets or bands upon the teeth. An alternate embodiment has the arch expander attaching directly to the palatal bone through screws placed through a grommet at the end of each shell by an orthodontist or oral surgeon.

5 Claims, 2 Drawing Sheets

MAXILLARY ARCH EXPANDER UNBANDED TO TEETH

CROSS REFERENCE TO RELATED APPLICATION

This non-provisional application claims priority to the pending non-provisional application for patent Ser. No. 10/439,638, filed May 16, 2003, now U.S. Pat. No. 7,094,051, which is commonly owned by the same inventor, and which is a continuation-in-part of application Ser. No. 10/186,604, filed Jul. 2, 2002, now U.S. Pat. No. 6,877,982 which is a continuation-in-part of application Ser. No. 09/975,633, filed Oct. 12, 2001, now U.S. Pat. No. 6,719,557, which is a continuation-in-part of application Ser. No. 09/750,527, filed Dec. 29, 2000, now U.S. Pat. No. 6,520,772, which is a continuation-in-part of application Ser. No. 09/598,766, filed Jun. 22, 2000, now U.S. Pat. No. 6,402,510, which is a continuation-in-part of application Ser. No. 09/406,426, filed Sep. 27, 1999, now U.S. Pat. No. 6,241,517, which is a continuation-in-part of application Ser. No. 09/143,071, filed Aug. 28, 1998, now U.S. Pat. No. 6,036,488, which in turn is a continuation-in-part of application Ser. No. 09/065,344, filed Apr. 23, 1998, now U.S. Pat. No. 5,919,042, which is related to application Ser. No. 08/526,686, filed Sep. 11, 1996, now U.S. Pat. No. 5,645,422, and related to Ser. No. 08/688,110, filed Jul. 29, 1996, now U.S. Pat. No. 5,769,631, all of which are incorporated herein by reference.

BACKGROUND OF THE INVENTION

This invention relates generally to orthodontic appliances for expanding the upper, or maxillary, jaw of a person. And more specifically the invention pertains to an expander connected to the jaw without using bands or crowns thus improving the appearance of a person's teeth when the present invention is installed for usage.

For many years, orthodontists have sought to correct the position of teeth for various reasons, including better chewing, better speech, hygiene, and appearance. Individual teeth can be rotated and translated into a new position. A tooth secures to the jaw with a periodontal ligament. Though extremely strong, the periodontal ligament can stretch as a tooth moves. Generally, a tooth is moved incrementally from an initial to a final position. Often the final position is along a defined arc.

Orthodontists have used many devices and therapies to move teeth. Common braces involve a wire secured to brackets or bands upon teeth. The brackets are adhered to the exterior face of a tooth or more recently to the interior face of a tooth. A wire then is placed upon the bracket and generally secured with small diameter elastic bands. The wire has an arcuate shape corresponding to the desired position of teeth. Wires are applied over time to the brackets with the wires becoming incrementally larger in diameter and hence more rigid. The rigidity of the wire gently orients a tooth to a new position. Brackets generally are used from the incisors rearward.

As teeth are to be moved, an orthodontist may have to create additional space along the jaw. Moving teeth rearward creates the space to accommodate teeth towards their final positions. An orthodontist applies bands to the molars and if needed, teeth forward of the molars. A band generally surrounds a tooth and is adhered to the tooth. The band has a fitting generally upon the exterior for securing the end of a wire used to establish a desired arc for the teeth. Bands also have sockets, generally horizontal, upon the exterior that cooperate with headgear. The headgear has interior rods that fit into the sockets and an outer bow joined to the interior rods. The outer bow connects to an adjustable strap that extends around the patient's neck. The strap provides a tension that is transferred into the bow and the interior rods to move the molars rearward thus opening space for other teeth to move. Teeth then move along the length of a jaw.

Additionally, an orthodontist may create space for teeth where a jaw is too narrow or more narrow than average. A jaw is widened by gently pushing apart molars outwards. Previously, molars were moved outwards using bands upon the rearmost molars connected to a threaded jack. The jack had a coaxial rod connected to a moving bar, or wing, and positioned by a threaded cylinder with keyholes. A patient would insert a key into the keyholes on a schedule prescribed by the orthodontist and turn the cylinder a prescribed rotation. Turning the cylinder urged the wings outwards and the jack against the molars to expand the jaw, generally the upper or maxillary jaw.

In recent years, orthodontia has developed mouth pieces that fit over teeth and direct teeth into new positions. The mouth pieces are translucent polymer material and fit upon existing teeth without the bands, wires, and brackets of previous methods. Invisalign® and other manufacturers provide mouth pieces, generally modeled in three dimensions by proprietary software for straightening teeth. The mouth pieces, similar to the prior art wires, gently move teeth incrementally over time. The mouth pieces can be worn during the daytime and are barely noticed by people other than a patient. An orthodontist prescribes the mouth pieces and the amount of tooth movement a given mouth piece induces. A mouth piece is generally held in place by friction between the mouth piece and the surface of the teeth. The mouth pieces perform well to align teeth along an arc, however the mouth pieces do not yet provide expansive lateral forces to widen a jaw.

Attempting to provide expansive lateral forces, the prior art connects an expansion device to a mouthpiece. The prior art utilizes vacuuming forming to connect an expansion device to a previously made mouthpiece. Further, an expansion device also joins to a mouthpiece as pelletized plastic or acrylic is placed intermittently upon the surface of a junction of the expansion device and a mouthpiece. The junction is then heated or chemically treated to make the pellets bond the expansion device to the mouthpiece.

SUMMARY OF THE INVENTION

The present invention provides an orthodontic arch expander joined to a mouthpiece proximate to the rear of the mouthpiece. The mouthpiece has a desired arc and a generally U shaped cross section to fit over the teeth of the upper jaw. The mouthpiece has two wings that join in the vicinity of the incisors and then become parallel and spaced apart in the vicinity of the molars. Near the molars upon the interior of the wings, an arch expander joins to the mouth piece. The arch expander has two telescoping shells with a threaded jack and cooperating springs. Each shell is joined to a corresponding wing of the mouthpiece. Turning the jack lengthens a rod that pushes the shells outwards against the mouthpiece thus widening the maxillary arch incrementally without brackets or bands upon the teeth. The invention also has an alternate embodiment where the arch expander attaches directly to the palatal bone. In the alternate embodiment, each of the telescoping shells has a grommet joined to an exterior end. The telescoping shells are oriented to expand laterally, generally between the left and right upper molars. A screw is then placed through each grommet and the screws are then turned into the palatal bone. An orthodontist or oral surgeon performs the installation of the screws into the bone.

Numerous objects, features and advantages of the present invention will be readily apparent to those of ordinary skill in the art upon a reading of the following detailed description of presently preferred, but nonetheless illustrative, embodiments of the present invention when taken in conjunction with the accompanying drawings. In this respect, before explaining the current embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and devices for carrying out the several purposes of the present invention. It is important, therefore, that the claims be regarded as including such equivalent constructions insofar as they do not depart from the spirit and the scope of the present invention.

It is, therefore, the principal object of this invention to provide an expander for widening the maxillary arch in a patient without permanently attaching to a patient's teeth.

Another object of the invention provides for a maxillary arch expander that provides laterally expanding forces but resists lengthening of the maxillary arch.

Yet another object of the invention provides for an orthodontic arch expander that includes a centrally disposed expansion apparatus operatively connected to the maxillary arch by a mouthpiece.

Yet another object of the invention provides for an orthodontic arch expander that includes a centrally disposed expansion apparatus operatively connected to the palatal bone by mechanical fasteners.

These and other objects may become more apparent to those skilled in the art upon review of the summary of the invention as provided herein, and upon undertaking a study of the description of its preferred embodiment, in view of the drawings.

BRIEF DESCRIPTION OF THE DRAWINGS

In referring to the drawings.

The same reference numerals refer to the same parts throughout the various figures.

DESCRIPTION OF THE PREFERRED EMBODIMENT

Figure 1:
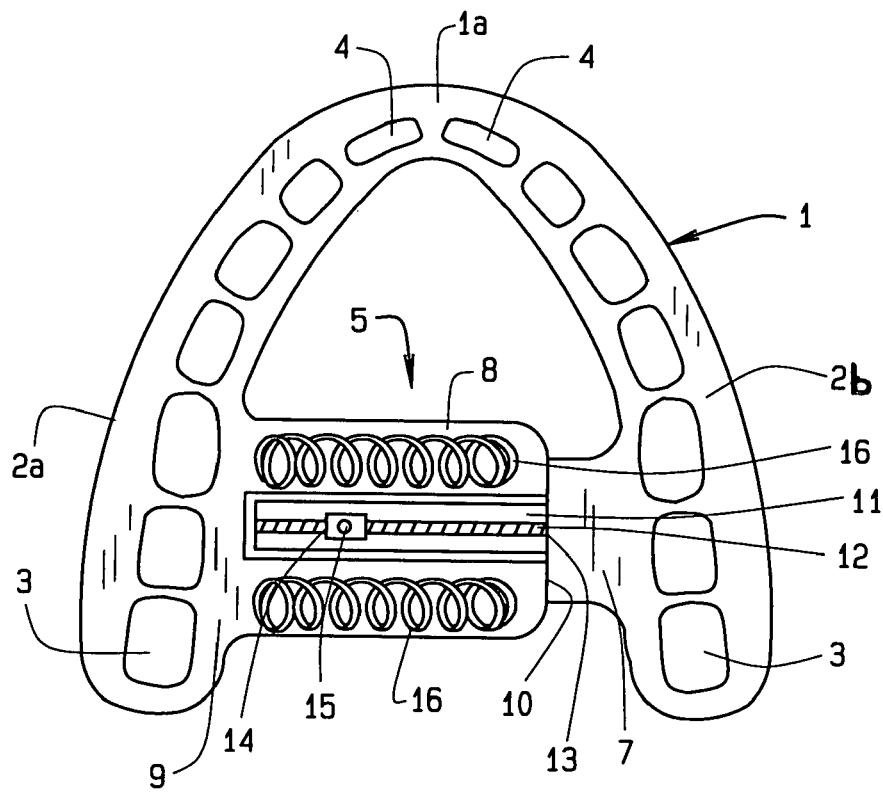
FIG. 1 shows an upward view of the invention installed upon the maxillary jaw using a mouthpiece.

In referring to the drawings, FIG. 1 shows the present invention installed about the teeth of the upper or maxillary jaw of a person. The present invention comprises a mouthpiece 1 generally arcuate in shape made of a polymer material, often transparent. The mouthpiece has two wings 2, left 2*a* and right 2*b*, that join at the midpoint 1*a* of the mouthpiece. A wing begins where it fits over a molar 3 and then curves and narrows forward toward where it fits over an incisor 4. The mouthpiece fits snugly upon the outside of the teeth. The mouthpiece has preprogrammed features that contact the teeth to straighten them as done with the Invisalign® series of mouthpieces. The wings have a generally U shape in cross section that is sized to fit snugly upon the various teeth in the jaw. The wings are modeled with computer programs for precise fit and sizing. The mouthpiece using the wings straightens teeth and moves them into a desired arcuate form. However, the wings of existing mouthpieces do not provide for lateral expansion of the arch by spacing apart the molars.

Within the wings shown in FIG. 1, the present invention has an expander 5 as originally shown in my previous application, Ser. No. 10/439,638 and which is incorporated herein by reference. The expander has a housing 6 with an advancing member 7 telescoping axially from within the housing. The housing joins to the left wing 2*a* shown in FIG. 1 proximate to where the left wing fits over the molars 3. The housing has a generally rectangular shape in cross section that extends across the width of at least two molars. The housing has side walls, a top 8, a bottom, a back 9 and an open front 10. A channel 11 extends rearward from the front edge of the outer housing. A threaded rod 12 extends forwardly from the housing back wall 9 to the front 10. The threaded rod extends along the center of the housing and rotates axially within the channel 11.

Then an advancing member 7 is slidably received within the housing 6. Opposite the housing, the advancing member joins to the right wing 2*b* of the mouthpiece. The member also has side walls, a bottom, a top, and a front wall 13 though of slightly less dimensions than the counterparts in the housing to permit fitting within the housing. A channel extends partially along the center of the top and cooperates with the channel in the housing to permit access therethrough to the threaded rod 12 within the housing.

Next, an internally threaded activation nut 14 operates upon the housing's threaded rod. The nut has a size so that its peripheral edge is accessible through the channels 11 of the housing and the advancing member. The nut has a plurality of radial holes 15 spaced upon in its periphery. The holes are also accessible through the channels using a key, or tool, (not shown) to rotate the nut thus moving it along the rod. The nut advances an activation wing (not shown) within the housing and towards the advancing member. The activation wing is located in front of the activation nut 14 for movement by it. The wing is journaled about the threaded rod and extends laterally to provide support for a spring 16 upon each end of the wing. The springs extend from the wing to the front wall of the advancing member. The springs provide an expansive force that moves the advancing member outwards and away from the housing. As can be appreciated, the springs supply their expansive force as the activation nut turns upon the rod. Turning of the nut 14 advances it along the rod 12 generally towards the center of the expander. The nut then moves the wing along with it, urging the springs to expand upon the advancing member. In doing so, the advancing member 7 and housing 6 impart lateral outward forces upon the molars 3 on each side of the maxillary jaw. Over time, the lateral forces widen the jaw as prescribed by the orthodontist.

Figure 2:
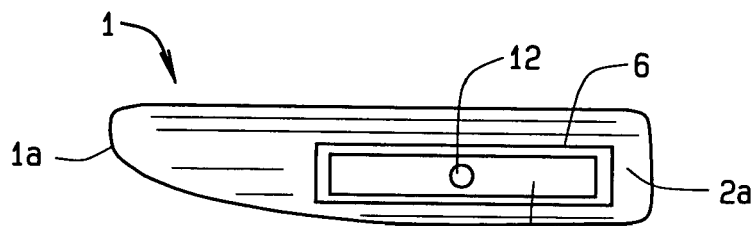
FIG. 2 shows a side view of the invention with the expander shown visible through the transparent mouthpiece.

Viewing the present invention from the side in FIG. 2, the mouthpiece has an apparent rectangular shape with rounded edges. The mouthpiece fits over the teeth of the maxillary jaw with the upper edge of the mouthpiece approaching the gum tissue. Here the left wing 2a of the mouthpiece is shown, extending from the incisors or midpoint 1a to the molars 3. The transparent mouthpiece shows the housing joined to the inner surface of the mouthpiece in the vicinity of the molars. The housing 6 has a generally rectangular cross section as previously described with the perimeter of the housing joining to the mouthpiece. The advancing member 7 nests within the housing and moves outward upon the wing as the nut turns upon the rod 12. The housing and the advancing member join to the mouthpiece by fusing to existing aligners by heating or chemical welding.

Figure 3:
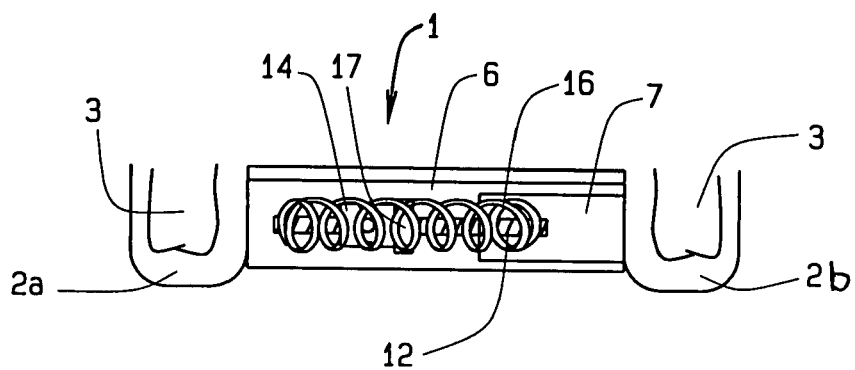
FIG. 3 shows an end view of the invention with the incisal edge towards the center and the molar ends of the invention towards the outside.

The operations of the present invention in cooperation with a mouthpiece 1 are shown via a rear view of the mouthpiece in FIG. 3. As previously described, the mouthpiece has a generally U shaped cross section so the left wing 2a and the right wing 2b fit over the teeth. The mouthpiece fits over the biting edge of the teeth and extends towards the gums. The housing joins to the left wing and the advancing member joins to the right wing, both proximate to the rear molars 3. The advancing member fits snugly within the housing. Springs 16 engage the advancing member outwards to expand the jaw. The springs extend into the expander onto a wing 17. The wing 17 as previously described is ahead of the activation nut 14. The nut 14 is turned upon the rod. In turning the nut, the expander converts the rotation of the nut into an axial expansive force transferred through the housing and the advancing member to expand the maxillary arch laterally.

Figure 4:
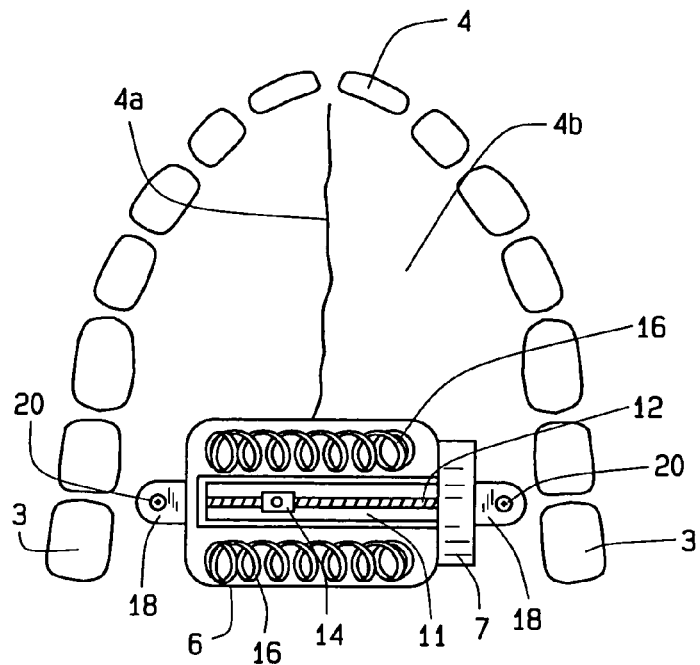
FIG. 4 shows an upward view of an alternate embodiment of the invention secured directly to the palatal bone; and, FIG. 5 describes a partially exploded view of the alternate embodiment.

An alternate embodiment of the expander is shown attached to the palate of a patient in FIG. 4, as an alternative to mounting the expander upon a mouthpiece. The maxillary jaw has teeth arranged in a generally arcuate shape with molars 3 towards the rear of the jaw and incisors 4 towards the front. The teeth are generally arranged symmetrically about a line 4a extending from between the two incisors to half way between the molars. This line follows the palate 4b, or upper roof of the mouth, of a patient. The palate is made of bone and is an integral part of the patient's skull. In younger patients and over longer durations in adult patients, bone can grow or be moved. The alternate embodiment utilizes the housing 6 and advancing member 7 along with internal hardware of rod 12, wing 17, activation nut 14, and springs 16 as previously described. The housing and advancing member each have a grommet 18 in the alternate embodiment. Each grommet has a generally round shape joined tangent to the back of the housing and the advancing member respectively. The plane of the grommet is generally parallel to the plane of the housing. Each grommet has a center hole 19 that seats a screw 20. Alternatively, the grommet is bent to conform to the surface of the patient's palate.

Figure 5:
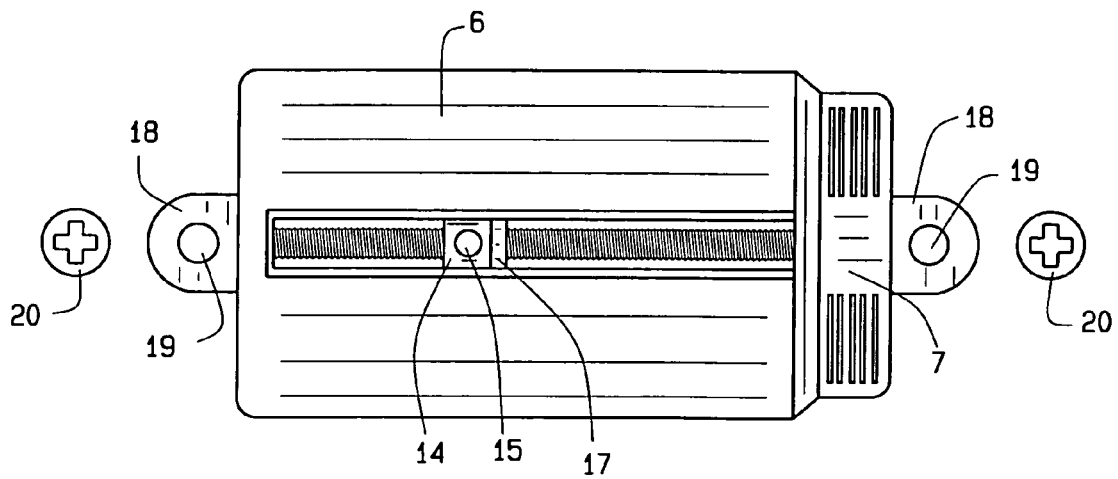

FIG. 5 shows the components of the alternate embodiment of the expander in a partially exploded view. The housing has a partially circular grommet joined to the back wall and the advancing member also has a partially circular grommet joined to its respective back wall. Each grommet has a rounded hole therethrough into which a screw turns for securement into the palatal bone during usage as later described. The grommets have a cross section along their circumference to permit snug seating of the screw upon the grommet thus reducing contamination by food and injury to the tongue by rough edges.

In use, the alternate embodiment is positioned by the oral surgeon, or orthodontist, between the molars with the channel facing towards the tongue. With the patient sedated, the channel of the assembled expander is oriented perpendicular to the molars and the expander is centered within the palate. The grommets provide a template for drilling pilot holes into the bone of the palate. The pilot holes are then cleaned and prepared to receive surgical grade screws. The grommets are then positioned over the pilot holes and the screws are installed singly until the grommets are snug upon the palate. Once the patient awakens, the patient is instructed on operating the expander and proper oral hygiene to keep the expander clean and to reduce the incidence of infection.

Variations or modifications to the subject matter of this development may occur to those skilled in the art upon review of the invention as described herein. Such variations, if within the spirit of this development, are intended to be encompassed within the scope of the invention as explained. The description of the preferred embodiment and as shown in the drawings, are set forth for illustrative purposes only to show the principle of this maxillary arch expander not attached to a patient's teeth.

I claim:

1. A device for incrementally widening the maxillary arch of the jaw of a person, said device adapting to rest upon the teeth of the maxillary arch without mechanical bands or adhesive bonds, and said device further comprising:
   a transparent mouthpiece having two wings placing over all of the teeth of said jaw each of said wings having a generally U shaped cross section;
   a housing having a generally hollow rectangular cross section including a top and an opposite bottom and two spaced apart and mutually parallel sidewalls, and said housing fusing by heat or chemical welding upon at least one of said top, said bottom, and said sidewalls to one of said wings upon the interior of the U shaped cross section;
   an advancing member having a generally hollow rectangular cross section of lesser dimension than said housing including a top and an opposite bottom and two spaced apart and mutually parallel sidewalls, and said advancing member fusing by heat or chemical welding upon at least one of said top, said bottom, and said sidewalls to the other of said wings upon the interior of the U shaped cross section and said advancing member extending telescopically in opposition to said housing;
   a threaded rod being generally centered in said device, turning and separating said housing outwards from said advancing member laterally within said maxillary arch; and,
   a pair of cooperating springs being parallel to said threaded rod and providing expansive force upon said housing and said advancing member thus easing turning of said threaded rod, and locating within said advancing member.

2. The device of claim 1 wherein said housing and said advancing member are located proximate to where said device fits upon the molars of said person.

3. A device for incrementally widening the maxillary arch of the jaw of a person, said device adapting to secure to palatal bone generally forming the roof of the mouth of said person, said device further comprising:
   a housing having a generally hollow rectangular cross section including a back wall and an opposite open front, a top and an opposite bottom and two spaced apart and mutually parallel sidewalls, and one grommet extending perpendicular to said back wall, said grommet having a hole locating upon the axis of the threaded rod; and,
   an advancing member having a generally hollow rectangular cross section of lesser dimension than said housing including a back wall and an opposite open front, a top and an opposite bottom and two spaced apart and mutually parallel sidewalls, telescoping from within said front of said housing and one grommet extending perpendicular to said back wall, said grommet having a hole therethrough locating upon the axis of the threaded rod;

at least two fasteners, said fasteners being placed through said holes in said grommets and adapting to insert into the palatal bone for securing said device to the person; and, a threaded rod being generally centered in said device, turning and separating said housing outwards from said advancing member laterally within said maxillary arch; and, a pair of cooperating springs being parallel to said threaded rod and providing expansive force easing turning of said threaded rod and biasing said advancing member and said housing outwardly;

whereby, turning said threaded rod separates said housing outwards from said advancing member laterally within said maxillary arch, widening the maxillary arch of a person's jaw.

4. The device of claim 3 further comprising:

said grommet upon said housing being parallel to the length of said housing and said hole through said grommet admitting said fastener perpendicular to the length of said housing; and, said grommet upon said advancing member being parallel to the length of said advancing member and said hole through said grommet admitting said fastener perpendicular to the length of said advancing member.

5. The device of claim 3 further comprising:

said grommet upon said housing being bent to fit the surface of the palatal bone and said hole through said grommet admitting said fastener perpendicular to the length of said housing; and, said grommet upon said advancing member being bent to fit the surface of the palatal bone and said hole through said grommet admitting said fastener perpendicular to the length of said advancing member.

* * * * *